(12) United States Patent
Kong et al.

(10) Patent No.: US 9,822,089 B2
(45) Date of Patent: Nov. 21, 2017

(54) R TYPE OF RESVERATROL DIMER, PREPARATION PROCESS THEREFOR AND PURPOSE THEREOF IN LOWERING BLOOD SUGAR LEVEL

(71) Applicant: CHINA PHARMACEUTICAL UNIVERSITY, Nanjing (CN)

(72) Inventors: Lingyi Kong, Nanjing (CN); Jianguang Luo, Nanjing (CN); Chao Han, Nanjing (CN); Xiaobing Wang, Nanjing (CN); Hao Hong, Nanjing (CN)

(73) Assignee: China Pharmaceutical University, Nanjing (CN)

( * ) Notice: Subject to any disclaimer, the term of this patent is extended or adjusted under 35 U.S.C. 154(b) by 0 days.

(21) Appl. No.: 15/024,858

(22) PCT Filed: Jun. 5, 2014

(86) PCT No.: PCT/CN2014/000558
§ 371 (c)(1),
(2) Date: Mar. 25, 2016

(87) PCT Pub. No.: WO2014/198123
PCT Pub. Date: Dec. 18, 2014

(65) Prior Publication Data
US 2016/0229828 A1    Aug. 11, 2016

(30) Foreign Application Priority Data
Jun. 14, 2013    (CN) .......................... 2013 1 0238137

(51) Int. Cl.
*C07D 307/80*    (2006.01)

(52) U.S. Cl.
CPC .................................. *C07D 307/80* (2013.01)

(58) Field of Classification Search
CPC ..................................................... C07D 307/80
See application file for complete search history.

(56) References Cited

U.S. PATENT DOCUMENTS

2011/0263518 A1*  10/2011  Lodder ................. A61K 31/05
                                                      514/25

FOREIGN PATENT DOCUMENTS

| CN | 101433534 A | 5/2009 |
| CN | 101977601 A | 2/2011 |
| CN | 103275044 A | 9/2013 |

OTHER PUBLICATIONS

Cichewicz et al. (J. Nat. Prod. 2000, 63, 29-33).*
Das et al. (Pharmaceutical Research 25(11)2008.*
He (J. of Chromatography A, 1151(1-2); 2007; 179-179.*

* cited by examiner

*Primary Examiner* — Shirley V Gembeh
(74) *Attorney, Agent, or Firm* — Muncy, Geissler, Olds & Lowe, P.C.

(57) ABSTRACT

The present invention relates to the field of natural pharmaceutical chemistry, and in particular, to a resveratrol dimer (7R,8R)-trans-δ-viniferin (I), a preparation process therefor and a purpose thereof in lowering a blood sugar level. According to the present invention, an R type of resveratrol dimer is separated from the resveratrol dimer by using high-speed countercurrent chromatography. Pharmacodynamic tests proved that the R type of resveratrol dimer has a better effect in lowering a blood sugar level than a racemate.

2 Claims, 3 Drawing Sheets

R TYPE OF RESVERATROL DIMER, PREPARATION PROCESS THEREFOR AND PURPOSE THEREOF IN LOWERING BLOOD SUGAR LEVEL

FIELD OF THE INVENTION

The present invention relates to the field of natural pharmaceutical chemistry, and in particular, to a resveratrol dimer (7R,8R)-trans-δ-viniferin, a preparation process therefor and a purpose thereof in lowering a blood sugar level.

DESCRIPTION OF RELATED ART

Separation of chiral compounds, especially chiral drugs is of importance in pharmaceutical research and pharmaceutical industry development. For drugs with a chiral center, pharmacological and toxicological actions thereof are different. In most cases, a stereisomer has a pharmacological effect, but a mirror molecular thereof has a very low pharmacological effect or even no pharmacological effect, or has a side-effect. In chiral separation technologies, high-performance liquid chromatography (HPLC) plays an extremely important role. However, a cost thereof is expensive and solvent consumption during preparative separation by using the HPLC method is also very great.

High-speed countercurrent chromatography is a novel technology to achieve separation and preparation based on that a sample has different distribution coefficients in two phases of a solvent that are not mutually solvable. Application of the countercurrent chromatography in separation of chiral compounds does not need to use a chemical means to bond a chiral reagent to a solid medium, but only needs to add a proper chiral reagent into a liquid-state stationary phase or mobile phase. A same countercurrent chromatography separation column can be used in separation of different chiral compounds for multiple times, which only needs to select a proper two-phase solvent system and chiral reagent. In addition, a same countercurrent chromatography column can be used in both chiral analysis and chiral preparative separation just by means of adjusting a quantity of the chiral reagent added into the stationary phase or mobile phase.

A compound trans-δ-viniferin (TVN for short) is a resveratrol dimer:

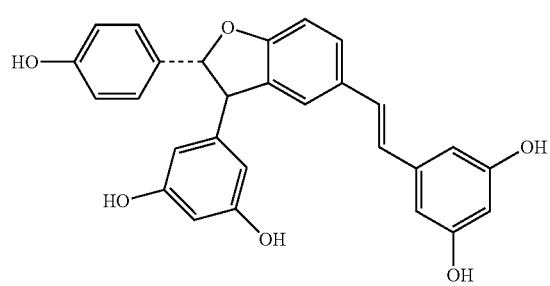

The compound is a natural product that was separated from grapes in 1977. Such compounds obtained by means of separation from a natural drug or a traditional Chinese medicine, are in a form of racemate. In laboratories, a TVN racemate may also be obtained by means of using *Momordica charantia* peroxidase to perform biotransformation of resveratrol.

At present, reports on activities of this compound are only limited to a strong anti-oxidative action. According to a patent (Publication No.: CN 101433534A) previously applied by us, it was found through in-vitro activity tests that, alpha-glucosidase inhibitory activity of the TVN racemate is 254 times of that of acarbose.

SUMMARY OF THE INVENTION

Technical Solution

The present invention discloses an optical isomer of TVN, namely, (7R,8R)-trans-δ-viniferin of a structural formula I, which is referred to as (R,R)-TVN for short, and has the following structural formula:

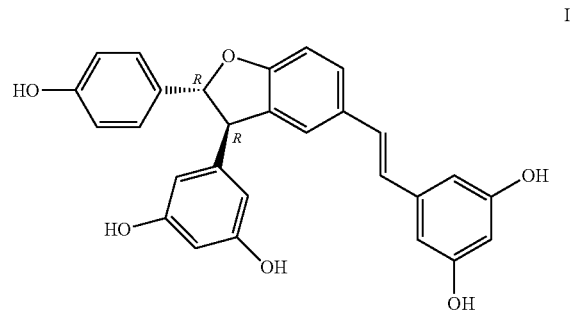

The present invention further discloses a chiral preparation process of (7R,8R)-trans-δ-viniferin of the structure formula I and a pharmaceutical purpose thereof.

Chiral separation is performed on a TVN racemate by using high-speed countercurrent chromatography (HSCCC), to obtain two optically pure compounds, (7R,8R)-trans-δ-viniferin(I,(R,R)-TVN) and ((7S,8S)-trans-δ-viniferin((S,S)-TVN).

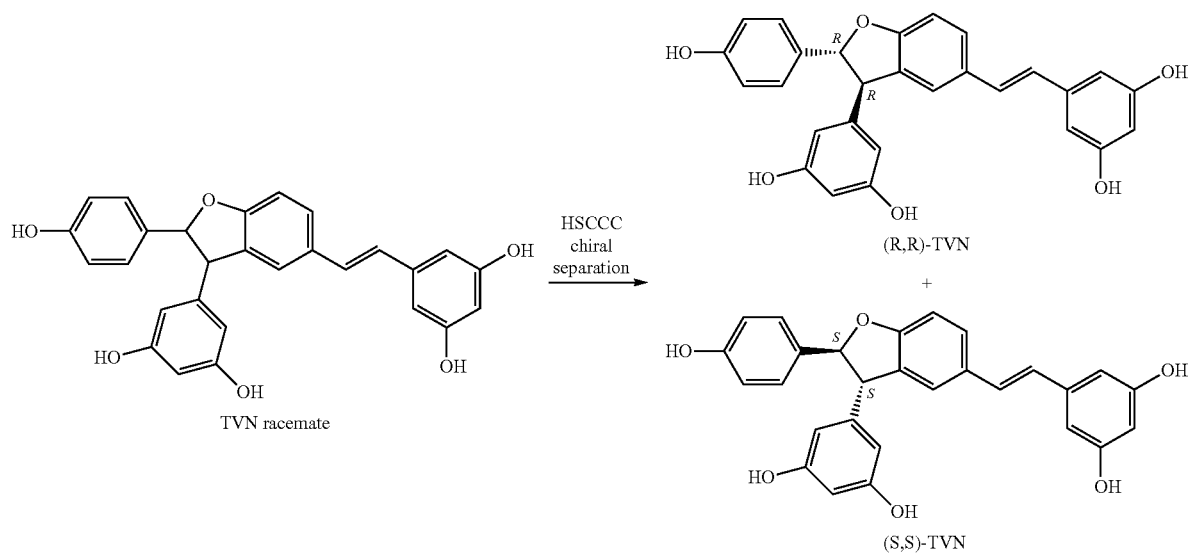

The compound of the structural formula I may be prepared by using the following process:

Biotransformation of resveratrol is performed by using *Momordica charantia* peroxidase, and a transformation product is washed by using chloroform and methanol as an eluent after a silica gel column chromatography process, and then passes through a preparative HPLC, to obtain a TVN racemate. After the TVN racemate passes through a high speed countercurrent chromatograph, two optically pure compounds, (R,R)-TVN and (S,S)-TVN can be obtained. An operational procedure of the high-speed countercurrent chromatograph includes: preparing a two-phase solvent by using n-hexane, ethyl acetate and water in a volume ratio of 4.8 to 5.2:4.8 to 5.2:9.8 to 10.2, where a top phase is a stationary phase, and 22 mmol/L to 28 mmol/L (2-hydroxypropyl)-β-cyclodextrin is added into a bottom phase to form a mobile phase; pumping the stationary phase into the high-speed countercurrent chromatograph from a top end thereof; simultaneously rotating a main machine until a pipeline is fully filled with the stationary phase and pumping the mobile phase thereinto; dissolving the TVN racemate into a small amount of the top phase when the mobile phase obviously flows from an outlet of the pipeline; then injecting a resulting solution to a sample cell, and starting to acquire data; and receiving target compositions according to peaks.

Results of pharmacodynamic tests show that, (R,R)-TVN can significantly lower a sucrose-induced high blood sugar level of a mouse, and has a better effect than the TVN racemate. However, an enantiomer thereof (S,S)-TVN cannot significantly lower a sucrose-induced high blood sugar level of a mouse.

Some pharmacodynamic tests and results thereof are as follows:

A mean body weight of mice was 22 g to 25 g. The mice were randomly divided into 6 groups, and each group included 10 animals. Each group of animals was intragastrically administered with a drug after 12 hours of fasting.

For a normal control group, a 0.5% CMC-Na solution whose volume is equal to that of a positive control group was administered.

For a negative control group, a 0.5% CMC-Na solution whose volume is equal to that of a positive control group was administered.

For an acarbose group, a 0.33 mg/ml acarbose suspension that was prepared by using a 0.5% CMC-Na solution was administered at a dosage of 0.3 ml per 10 g of weight.

For a TVN racemate group, a 0.33 mg/ml TVN racemate suspension that was prepared by using a 0.5% CMC-Na solution was administered at a dosage of 0.3 ml per 10 g of weight.

For a (S,S)-TVN group, a 0.33 mg/ml (S,S)-TVN suspension that was prepared by using a 0.5% CMC-Na solution was administered tat a dosage of 0.3 ml per 10 g of weight.

For a (R,R)-TVN group, a 0.33 mg/ml (R,R)-TVN suspension that was prepared by using a 0.5% CMC-Na solution was administered at a dosage of 0.3 ml per 10 g of weight.

After 30 min, animals in the groups other than the normal group were intragastrically administered with a 6.7% sucrose solution at a dosage of 0.3 ml per 10 g of weight, and animals in the normal group were intragastrically administered with water whose volume is equal to that of the sucrose solution. Orbital blood sampling was separately performed at four time points, namely 0 h, 0.5 h, 1 h, and 2 h after intragastric administration of the sucrose solution to the animals. Then, 2 μL of blood serum was taken after centrifugation and added into a 96-pore plate. Thereafter, 200 μL of a reagent from a glucose assay kit was further added thereinto and a 505 nm micro-plate reader was used to measure a value of absorbance. A blood sugar concentration was obtained from a standard curve. Refer to the table below:

| Group | Blood sugar concentration (mmol/L) ($x \pm s$, n = 10) | | | |
|---|---|---|---|---|
| | 0 h | 0.5 h | 1 h | 2 h |
| Blank control group | 6.67 ± 1.06 | 6.90 ± 1.06** | 6.47 ± 1.29** | 7.22 ± 0.58 |
| Negative control group | 8.47 ± 1.24 | 12.02 ± 1.67 | 10.62 ± 1.65 | 8.71 ± 1.44 |

-continued

| | Blood sugar concentration (mmol/L) (x ± s, n = 10) | | | |
|---|---|---|---|---|
| Group | 0 h | 0.5 h | 1 h | 2 h |
| Acarbose group | 7.94 ± 1.25 | 9.74 ± 1.45* | 8.32 ± 1.50* | 8.54 ± 1.04 |
| TVN racemate group | 7.75 ± 1.57 | 10.34 ± 1.75* | 9.07 ± 1.55* | 8.83 ± 1.46 |

*P < 0.05;
**P < 001 (relative to a negative control group)

A sucrose tolerance test curve was drawn, and an area under the curve was calculated, as shown in FIG. 1.

All data was represented by using a mean value±a standard deviation ($\bar{x}$±s). SPSS11.5 software was used for analysis, and data comparison was performed by means of a one-way analysis of variance. P<0.05 represents that there was a significant difference; and P<0.01 represents that there was an extremely significant difference.

According to a table of blood sugar level change in an orally-administered sucrose tolerance test for normal mice, calculation was performed by using the SPSS11.5 software. Compared with the negative control group, blood glucose-lowering rates of the acarbose group and the TVN racemate group at 0.5 h were respectively 18.97% and 13.98%, and P<0.05, which means that there was a significant difference. Compared with the negative control group, blood glucose-lowering rates thereof were respectively 21.66% and 14.60% at 1 h, which means that there was a significant difference. Compared with the negative control group, blood glucose-lowering rates of the (R,R)-TVN group at 0.5 h and 1 h were respectively 30.20% and 22.79%, and P<0.01, which means that there was an extremely significant difference. Compared with the negative control group, blood glucose-lowering rates of the (S,S)-TVN group were respectively 0.08% and 3.01% at 0.5 h and 1 h, which had almost no difference from that of the negative control group.

In FIG. 1, a general sucrose tolerance level in the test was studied by means of calculating the area under the sucrose tolerance test curve. Compared with the negative control group, the areas under the sucrose tolerance test curves of the TVN racemate group, the (R,R)-TVN group and the negative control group were respectively 18.3 mmol h/L, 16.7 mmol h/L and 21.0 mmol h/L, and P<0.01, which means that there was an extremely significant difference. The area under the sucrose tolerance test curve of the (S,S)-TVN group was 20.9 mmol h/L, which had almost no difference from that of the negative control group.

Advantageous Effect

Conclusions: (R,R)-TVN can significantly lower a sucrose-induced high blood sugar level of a mouse, but an enantiomer thereof (S,S)-TVN cannot significantly lower a sucrose-induced high blood sugar level of a mouse. Moreover, a mixture of (R,R)-TVN and (S,S)-TVN, namely a TVN racemate has a hypoglycemic activity between hypoglycemic activities of the both.

DETAILED DESCRIPTION OF THE INVENTION

Embodiment 1

Separation of a TVN racemate by high-speed countercurrent chromatography:

Preparation of a sample solution: 20 mg of a TVN racemate was dissolved in 10 mL of a top organic phase.

Figure 1:
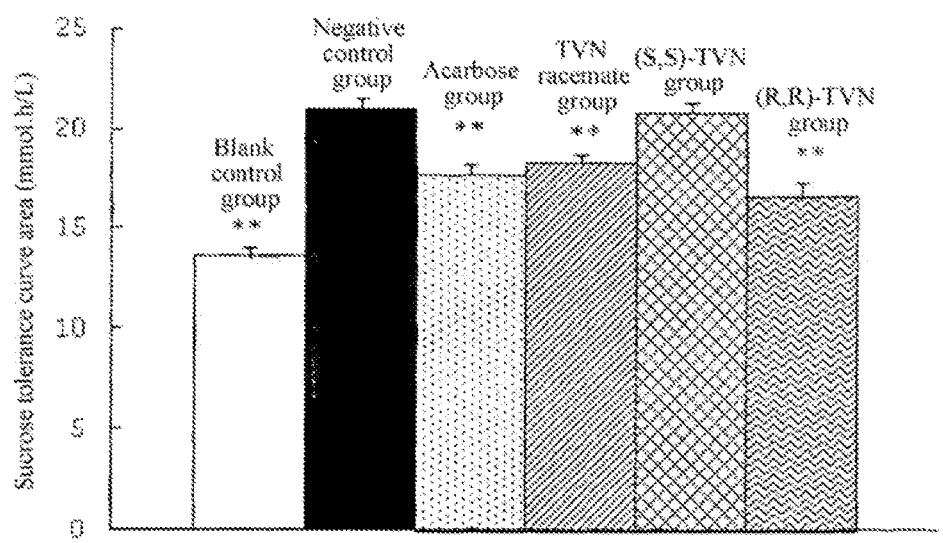
FIG. 1 is a diagram of an area under a sucrose tolerance test curve for each test group, where: "*": P<0.05; "**": P<0.01 (relative to a negative control group)
Figure 2:
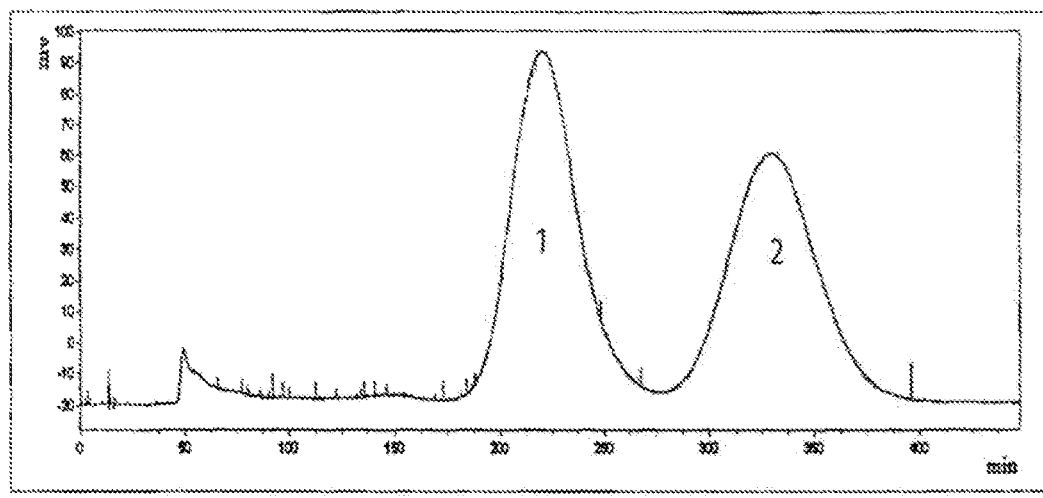
FIG. 2 is a diagram of separation of a TVN racemate by high-speed countercurrent chromatography.

1,200 mL of a two-phase solvent system consisting of n-hexane, ethyl acetate and 25 mmol/L aqueous solution of (2-hydroxypropyl)-β-cyclodextrin in a volume ratio of 5:5:10 was placed in a 2,000 mL separating funnel for full equilibrium overnight, then separated and ultrasonically processed for 30 min. A top-phase solvent was used as a stationary phase, and injected into a high-speed countercurrent chromatograph at a flow rate of 30 ml/min until an entire pipeline system was filled. A main machine was rotated at a constant rotation rate of 800 r/min. A column oven was started to maintain a temperature at 5° C. A bottom-phase solvent was used as a mobile phase, and the bottom phase was injected into the high-speed countercurrent pipeline at a rate of 1 mL/min. When the bottom phase obviously flowed from an outlet of the pipeline, the sample solution was injected to a mouth of a sample cell, and fractions were collected under ultraviolet detection at 313 nm. For a countercurrent diagram, refer to FIG. 2, where: 1 represents (S,S)-TVN, and 2 represents (R,R)-TVN. To the collected samples, a small amount of hydrochloric acid was added for acidification, and a resulting solution was extracted with ethyl acetate for 3 times, and then vacuum concentrated to obtain a crude product. After a silica gel column chromatography process, the crude product was eluted by using dichloromethane and methanol in a volume ratio of 15:1 to remove a small amount of (2-hydroxypropyl)-β-cyclodextrin, and obtain high purity samples, i.e. 8.2 mng of (S,S)-TVN and 9.4 mg of (R,R)-TVN. A recovery rate exceeded 80%.

Figure 3:
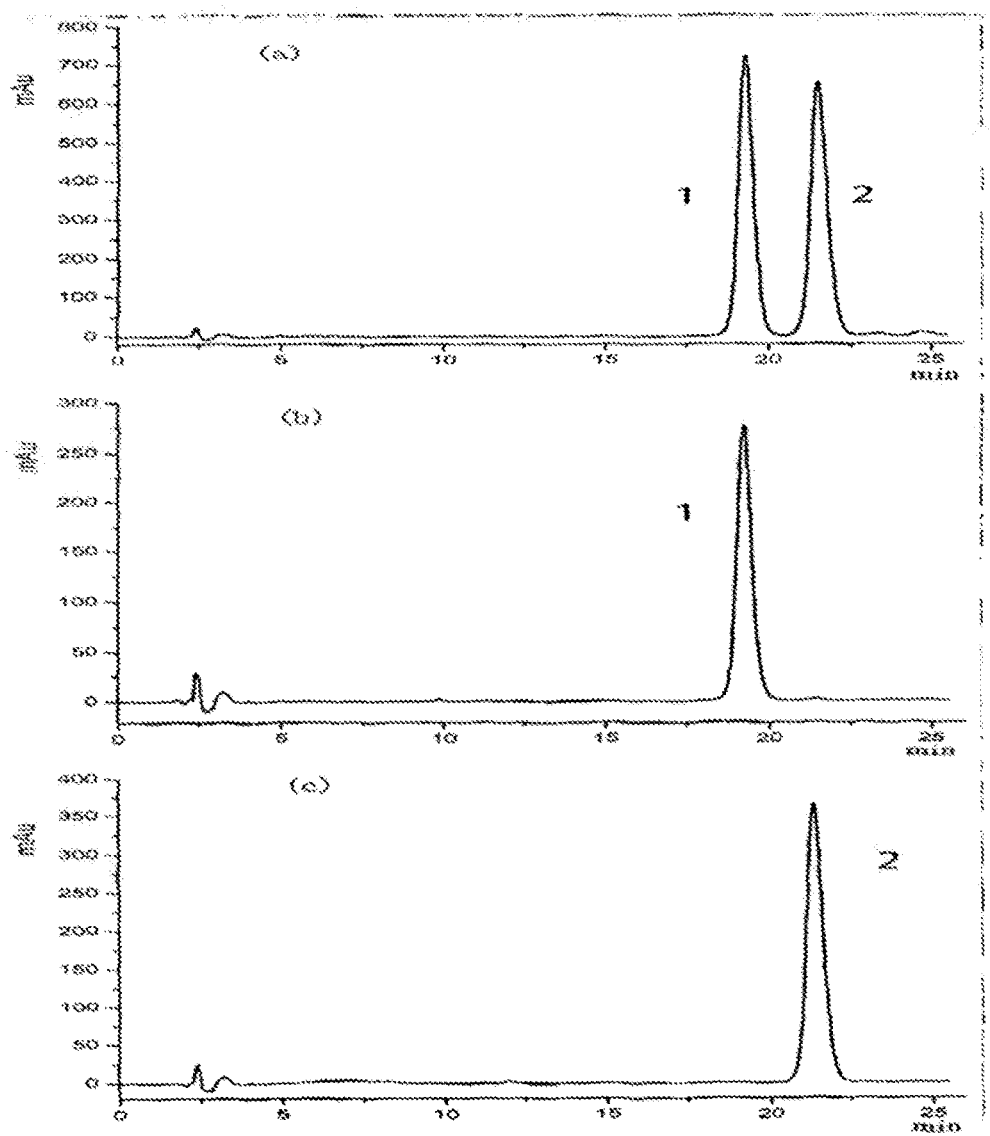
FIG. 3 is HPLC diagrams of a TVN racemate and HSCCC fractions.

The (R,R)-TVN and (S,S)-TVN may be verified by using the following method:

The TVN racemate and two HSCCC fractions were verified by using HPLC, as shown in FIG. 3. In FIG. 3, (a) represents the TVN racemate; (b) represents HSCCC including a fraction of (S,S)-TVN; and (c) represents HSCCC including a fraction of (R,R)-TVN. HPLC conditions: an Agilent HPLC workstation was set by using Agilent 1200 HPLC, and a chromatographic column was Agilent Zorbax SB-C18: column (4.6 mm*250 mm, 5 μm), temperature: 30° C., mobile phase: 25 mmol L-1 HP-β-CD aqueous solution and acetonitrile (75:25, v/v), flow rate: 1.0 mL min-1, and detection wavelength: 320 nm.

In FIG. 3, a retention time (t=21.493 min) of (R,R)-TVN is longer than a retention time (t=19.247 min) of (S,S)-TVN. In addition, purities of two compounds both exceed 98%, and values of enantiomer excess (ee) thereof reach 100%.

Figure 4:
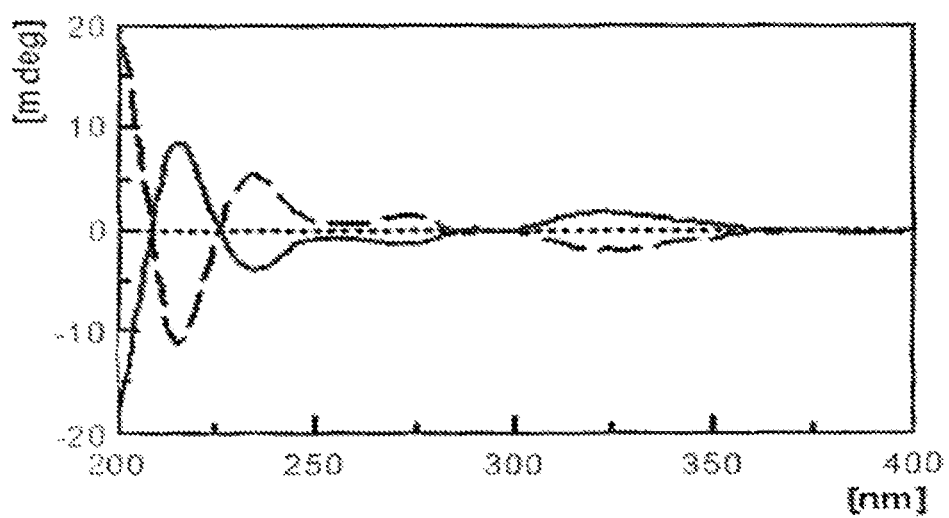
FIG. 4 is a CD diagram of two HSCCC fractions.

FIG. 4 is a circular dichroism (CD) spectrum diagram of two compounds. When the two compounds have a same concentration, CD curves thereof are almost completely symmetric. In the figure, a dotted line shows a CD diagram of HSCCC including a fraction of (S,S)-TVN; and a solid line shows a CD diagram of HSCCC including a fraction of (R,R)-TVN, where concentrations thereof are both 0.2 mg/ml.

What is claimed is:

1. A process for preparing a resveratrol dimer (7R,8R)-trans-δ-viniferin in structural formula (I), comprising: preparing a two-phase solvent by using n-hexane, ethyl acetate and water in a volume ratio of 5:5:10, wherein a top phase is a stationary phase, and 22 mmol/L to 28 mmol/L (2-hydroxypropyl)-(β-cyclodextrin is added into a bottom phase to form a mobile phase; pumping the stationary phase into a high-speed countercurrent chromatograph from a top end thereof; simultaneously rotating a main machine until a pipeline is fully filled with the stationary phase and pumping the mobile phase thereinto; dissolving a racemate into a small amount of the top phase when the mobile phase obviously flows from an outlet of the pipeline; then injecting a resulting solution into a sample cell and starting to acquire data; and receiving target compositions according to peaks, to obtain the compound

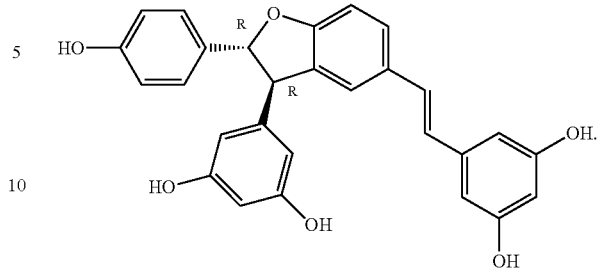

I

2. A method for lowering high blood sugar level, comprising administering a subject with a suspension of resveratrol dimer (7R,8R)-trans-δ-viniferin in structural foimula (I)

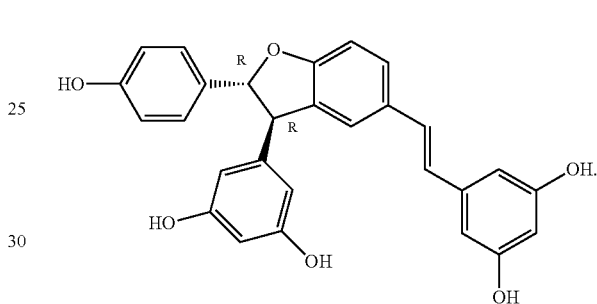

I

* * * * *